:

US009383352B2

(12) United States Patent
Nagalla et al.

(10) Patent No.: US 9,383,352 B2
(45) Date of Patent: Jul. 5, 2016

(54) SALIVARY PROTEIN GLYCOSYLATION TEST FOR DIAGNOSIS AND MONITORING OF DIABETES

(71) Applicant: DiabetOmics, LLC, Hillsboro, OR (US)

(72) Inventors: Srinivasa R. Nagalla, Hillsboro, OR (US); Eric S. Bean, Wilsonville, OR (US)

(73) Assignee: Diabetomics, Inc., Hillsboro, OR (US)

( * ) Notice: Subject to any disclaimer, the term of this patent is extended or adjusted under 35 U.S.C. 154(b) by 0 days.

(21) Appl. No.: 14/226,131

(22) Filed: Mar. 26, 2014

(65) Prior Publication Data

US 2015/0276723 A1 Oct. 1, 2015

(51) Int. Cl.
G01N 33/52 (2006.01)
G01N 33/68 (2006.01)
G01N 33/66 (2006.01)
G01N 21/78 (2006.01)

(52) U.S. Cl.
CPC .............. *G01N 33/525* (2013.01); *G01N 33/66* (2013.01); *G01N 33/6872* (2013.01); *G01N 21/78* (2013.01); *G01N 2800/042* (2013.01); *G01N 2800/56* (2013.01); *Y10T 436/143333* (2015.01); *Y10T 436/144444* (2015.01); *Y10T 436/200833* (2015.01)

(58) Field of Classification Search
CPC ........... Y10T 436/143333; Y10T 436/144444; Y10T 436/19; Y10T 436/193333; Y10T 436/20; Y10T 436/200833; G01N 21/77; G01N 21/78; G01N 33/48; G01N 33/66; G01N 33/6872; G01N 33/525; G01N 2800/042; G01N 2800/56

USPC ......... 436/63, 87, 94, 95, 124, 125, 127, 128, 436/164, 166, 169, 170; 435/14, 287.7, 435/287.8, 288.7; 422/400, 420, 421, 422/82.05, 430
See application file for complete search history.

(56) References Cited

U.S. PATENT DOCUMENTS

| 5,258,501 | A | * | 11/1993 | Barbaric et al. | ............... 530/395 |
| 8,476,008 | B2 | * | 7/2013 | Nagalla et al. | ............... 435/4 |
| 2003/0004403 | A1 | | 1/2003 | Drinan et al. | |
| 2006/0099326 | A1 | * | 5/2006 | Keogh et al. | ............... 427/2.26 |

(Continued)

FOREIGN PATENT DOCUMENTS

JP 2003254959 * 9/2003
WO 2010/132447 11/2010

OTHER PUBLICATIONS

Spiro, R. G., "Protein glycosylation: nature, distribution, enzymatic formation, and disease implications of glycopeptide bonds", Glycobiology, vol. 12, No. 4, 43R-56R, 2002, 14 pages.

(Continued)

Primary Examiner — Maureen Wallenhorst
(74) Attorney, Agent, or Firm — Schwabe Williamson & Wyatt

(57) ABSTRACT

Disclosed herein are methods and tests for diagnosing and/or monitoring a metabolic condition such as diabetes in a subject, wherein the methods and tests measure salivary glycoproteins. Some of the methods are based on the oxidation of glycoproteins in a sample from the subject, such as saliva or urine, for example using sodium metaperiodate, and then detecting the aldehydes generated during oxidation using a chemical detection method. Also disclosed are kits and lateral flow devices for detecting glycoproteins in a saliva sample.

19 Claims, 14 Drawing Sheets

Saliva Test Strip for Screening & Monitoring Diabetes Control side view top view bottom view

(56) References Cited

U.S. PATENT DOCUMENTS

2009/0074613 A1* 3/2009 Kaindl et al. ............... 422/57
2009/0206245 A1* 8/2009 Nagahori et al. ........... 250/282

OTHER PUBLICATIONS

Lau et al., "Complex N-Glycan Number and Degree of Branching cooperate to Regulate Cell proliferation and Differentiation", Cell No. 129: 123-134, DOI 10.1016/j.cell.2007.01.049, 2007, 12 pages.
Dennis et al., "Metabolism, Cell Surface Organization, and Disease", Cell No. 139:12291241, DOI 10.1016/j.cell.2009.12.008, 2009, 13 pages.
Riedl et al., "N-Glycosylation of Carnosinase Influences Protein Secretion and Enzyme Activity", Diabetes, 59:1984-1990, Aug. 2010, 7 pages.
Weigert et al., "Palmitate-Induced Activation of the Hexosamine Pathway in Human Myotubes", Diabetes, 52:650-656, Mar. 2003, 7 pages.
Streckfus et al., "Salivary Glands and Saliva, No. 3: Saliva as a diagnostic fluid", Oral Diseases, 8:69-76, 2002, 8 pages.
Malamud, "Salivary Diagnostics: The future is now", JADA, 137:284-286, Mar. 2006, 2 pages.
Tabak, "Point-of-Care Diagnostics Enter the Mouth", Annals of The New York Academy of Sciences 1098: 7-14, 2007, 8 pages.
Rao et al., "Proteomic Identification of Salivary Biomarkers of Type-2 Diabetes", Journal of Proteome Research vol. 8, No. 1, pp. 239-245, 2009, 7 pages.
Kovatchev et al., "Symmetrization of the Blood Glucose Measurement Scale and Its Applications", Diabetes Care, vol. 20, No. 11, Nov. 1997, pp. 1655-1658, 4 pages.
Clarke et al., "Statistical Tools to Analyze Continuous Glucose Monitor Data", Diabetes Technology & Therapeutics, vol. 11, Supplement 1, 2009, DOI: 10.1089/dia.2008.0138, pp. S-45-S-54, 19 pages.
Shrout et al., "Intraclass Correlations: Uses in Assessing Rater Reliability", Psychological Bulletin, vol. 86, No. 2, 1979, pp. 420-428, 9 pages.
European Application No. 15160916.1 Extended European Search Report dated Aug. 3, 2015, 10 pages.
Belce, A. et al., "Evaluation of Salivary Sialic Acid Level and Cu—Zn Superoxide Dismutase Activity in Type 1 Diabetes Mellitus", Tohoku Journal of Experimental Medicine, Tohoku University Medical Press, Sendai, JP, vol. 192, No. 3, Dec. 1, 2000, pp. 219-225.
Warren, Leonard, "The Thiobarbituric Acid Assay of Sialic Acids", The Journal of Biological Chemistry, vol. 234, No. 8, Aug. 1, 1959, pp. 1971-1975.
Sashikumar, R. et al., "Salivary Glucose Levels and Oral Candidal Carriage in Type II Diabetics", Oral Surgery, Oral Medicine, Oral Pathology, Oral Radiology and Endodontics, Mosby-Year Book, St. Louis, MO, US, vol. 109, No. 5, May 1, 2010, pp. 706-711.
Mata, Antonio D. et al., "Effects of Diabetes Mellitus on Salivary Secretion and its Composition in the Human", Molecular and Cellular Biochemistry, Feb. 22, 2004, 6 pages.
Rasanen, Juha P. et al., "Glycosylated Fibronectin as a First-Trimester Biomarker for Prediction of Gestational Diabetes", Obstetrics and Gynecology, vol. 122, No. 3, Sep. 1, 2013, pp. 586-594 (Abstract).
Rao, Paturi V. et al., "Salivary Protein Glycosylation as a Noninvasive Biomarker for Assessment of Glycemia", Journal of Diabetes Science and Technology, 1-8, Oct. 9, 2014, 8 pages.

\* cited by examiner

Periodate Oxidation of Vicinal Diols Generates Aldehydes

Sialic acid and fucose most readily oxidized under the conditions employed for saliva

4-amino-3-hydrazino-5-mercapto-1,2,4-triazole reactivity with aldehydes (AHMT)

Salivary Total Glycosylation – Plate Assay

Prototype Solid Phase Assay
1. AHMT immobilized on membrane
2. Oxidize sample externally, add 20 μL
3. Add 25 μL 2 N NaOH

Dipstick Standard Curve

Comparison of Plate & Dipstick Assays Using Saliva Samples

Two-Membrane Dipstick Test

- 2 membrane device (AHMT + alkali)
- External oxidation (30 sec)
- Add sample, read after 5 min

Saliva Test Strip for Screening & Monitoring Diabetes Control

Evaluation of three-membrane (one-step) saliva test strip
(% Reflectance)

| Fetuin mg/mL | Sodium periodate concentration (mg/10mL of buffer) | | |
|---|---|---|---|
| | 30 | 50 | 100 |
| 0 | 49.74 | 35.27 | 28.31 |
| 5 | 23.53 | 23.85 | 19.01 | ance with various embodiments;

SALIVARY PROTEIN GLYCOSYLATION TEST FOR DIAGNOSIS AND MONITORING OF DIABETES

GOVERNMENT INTERESTS

This invention was made with Government support under Grant/Contract No. R43 DE020973 awarded by the National Institutes of Health. The Government has certain rights in the invention.

TECHNICAL FIELD

Embodiments herein relate to the field of diabetes, and more specifically to the diagnosis and monitoring of subjects who have pre-diabetes, diabetes, or diabetic complications.

BACKGROUND

The elevated glucose levels seen in pre-diabetes, gestational diabetes, and established diabetes can affect protein biomarkers found in biological fluids. For example, glycemic control may affect direct, non-enzymatic protein glycation in which glucose becomes covalently linked to target proteins through the formation of a Schiff base between the aldehyde group of the glucose molecule and the amino group of a lysine residue in a protein. The Schiff base then undergoes an Amadori rearrangement and oxidation to form an advanced glycation end product. One example of an advanced glycation end product is hemoglobin A1c (HbA1c). The blood levels of HbA1c represent the average blood glucose (BG) level over the previous 3 months, reflecting the lifespan of the red blood cells that carry hemoglobin.

There are a number of issues that arise with using HbA1c to monitor glucose homeostasis, including its inability to reflect shorter-term variations in BG, significant genetic and non-glycemic effects on HbA1c levels, and significant age-dependent and ethnic variations in the relationship between HbA1c levels and average BG levels. The use of glycated albumin or fructosamine as an alternative offers the advantage of reflecting a shorter response time (e.g., representing the average BG level over the previous 2-4 weeks), but the effects of the various factors that hamper the utility of HbA1c on the relationship between these glycated proteins and previous BG levels remain problematic.

BRIEF DESCRIPTION OF THE DRAWINGS

Embodiments of the present disclosure will be readily understood by the following detailed description in conjunction with the accompanying drawings. Embodiments are illustrated by way of example and not by way of limitation in the figures of the accompanying drawings.

DETAILED DESCRIPTION

Figure 1A:
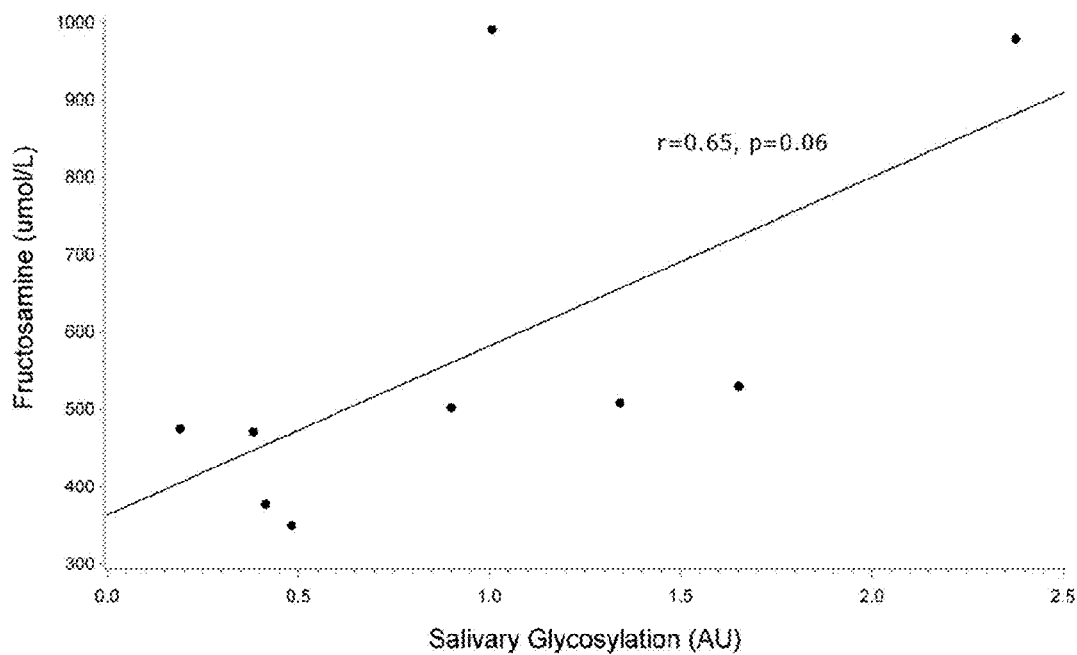
FIGS. 1A and 1B are graphs illustrating the relationship of baseline salivary glycosylation with fructosamine (FIG. 1A) and hemoglobin A1c (FIG. 1B), in accordance with various embodiments.

In the following detailed description, reference is made to the accompanying drawings which form a part hereof, and in which is shown by way of illustration embodiments in which the disclosure may be practiced. It is to be understood that other embodiments may be utilized and structural or logical changes may be made without departing from the scope of the present disclosure. Therefore, the following detailed description is not to be taken in a limiting sense, and the scope of embodiments in accordance with the present disclosure is defined by the appended claims and their equivalents.

Various operations may be described as multiple discrete operations in turn, in a manner that may be helpful in understanding embodiments of the present disclosure; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present disclosure.

For the purposes of the present disclosure, the phrase "A/B" means A or B. For the purposes of the present disclosure, the phrase "A and/or B" means "(A), (B), or (A and B)". For the purposes of the present disclosure, the phrase "at least one of A, B, and C" means "(A), (B), (C), (A and B), (A and C), (B and C), or (A, B and C)". For the purposes of the present disclosure, the phrase "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In order to facilitate review of the various embodiments of this disclosure, the following explanations of specific terms are provided:

As used herein, the term "analyte" refers to an atom, molecule, group of molecules, or compound of natural or synthetic origin (e.g., aldehydes, glycolipids, or glycoproteins) sought to be detected or measured. Analytes may include, but are not limited to aldehydes, antibodies, drugs, hormones, antigens, haptens, glycoproteins, glycolipids, carbohydrates, apoproteins, and cofactors.

As used herein, the term "biological sample" refers to any sample obtained from a plant or animal subject. As used herein, biological samples include all clinical samples useful for detection of glycosylation profile, protein amount, or glycosylation pattern of proteins in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; mucus; saliva; milk; skin scrapes; surface washings; urine; sputum; sweat; semen; vaginal secretion; fluid from ulcers and/or other surface eruptions, blisters, abscesses, and/or extracts of tissues; cells or organs; cerebrospinal fluid; prostate fluid; pus; or bone marrow aspirates. The biological sample may also be a laboratory research sample such as a cell culture supernatant. In particular examples, the sample is urine or saliva. The sample may be collected or obtained using methods well known to those skilled in the art.

As used herein, the term "chemically oxidizing" refers to a process that involves deliberately contacting a biological sample, such as a saliva sample, with a chemical oxidizing reagent. As used herein, the term "chemically oxidizing" excludes naturally occurring oxidizing processes, such as those that occur when biological samples are exposed to oxygen, such as may be present in ambient air. Rather, the term encompasses chemical oxidizing processes resulting from deliberate contact with a solid or liquid oxidizing agent. Generally, such chemical oxidation results in all or most of the sialic acid and/or fucose in the sample becoming oxidized, such as at least 50%, at least 70%, at least 90%, or even more of the sialic acid and/or fucose present in the sample becoming oxidized.

As used herein, the term "detecting" refers to quantitatively or qualitatively determining the presence of the analyte(s) under investigation, such as a glycoprotein or an aldehyde.

As used herein, the term "diabetes mellitus" refers to a disease caused by a relative or absolute lack of insulin leading to uncontrolled carbohydrate metabolism, commonly simplified to "diabetes," though diabetes mellitus should not be confused with diabetes insipidus. As used herein, "diabetes" refers to diabetes mellitus, unless otherwise indicated. A "diabetic condition" includes pre-diabetes and diabetes. Type 1 diabetes (sometimes referred to as "insulin-dependent diabetes" or "juvenile-onset diabetes") is an auto-immune disease characterized by destruction of the pancreatic β cells that leads to a total or near total lack of insulin. In type 2 diabetes (T2DM; sometimes referred to as "non-insulin-dependent diabetes" or "adult-onset diabetes"), the body does not respond to insulin, though it is present. As used herein, the term "metabolic condition" is used to refer to type 1 diabetes, type 2 diabetes, pre-diabetes, and diabetes complications.

Symptoms of diabetes include: excessive thirst (polydipsia); frequent urination (polyuria); extreme hunger or constant eating (polyphagia); unexplained weight loss; presence of glucose in the urine (glycosuria); tiredness or fatigue; changes in vision; numbness or tingling in the extremities (hands, feet); slow-healing wounds or sores; and abnormally high frequency of infection. Diabetes may be clinically diagnosed by a fasting plasma glucose (FPG) concentration of greater than or equal to 7.0 mmol/L (126 mg/dL), or a plasma glucose concentration of greater than or equal to 11.1 mmol/L (200 mg/dL) at about two hours after an oral glucose tolerance test (OGTT) with a 75 g load. A more detailed description of diabetes may be found in *Cecil Textbook of Medicine*, J. B. Wyngaarden, et al., eds. (W.B. Saunders Co., Philadelphia, 1992, 19$^{th}$ ed.).

As used herein, the term "glycosylation" refers to covalent modification of a biomolecule (such as a protein or lipid) with one or more oligosaccharide chains. Proteins having at least one oligosaccharide modification are referred to as "glycoproteins" or "glycosylated proteins." In the case of proteins, glycosylation is usually N-linked or O-linked. N-linked glycosylation refers to linkage of an oligosaccharide to the side chain amino group of an asparagine residue in a protein. O-linked glycosylation refers to linkage of an oligosaccharide to the hydroxyl side chain of a serine, threonine, or hydroxylysine amino acid in a protein.

The oligosaccharide chains of glycoproteins are enormously varied, due to the combination of various sugars (for example, N-acetylglucosamine, N-acetylgalactosamine, N-acetyllactosamine, mannose, galactose, glucose, N-acetylneuraminic acid, or fucose) and the presence of branched structures (such as biantennary, triantennary, or tetra-antennary structures).

As used herein, the term "lateral flow device" refers to a device that absorbs or adsorbs a liquid sample, routes that liquid sample to a detection zone, and uses a detection method to generate a detectable signal in response to the presence or absence of a specific analyte (such as a glycoprotein, glycolipid, or aldehyde). The device may be a test strip used in lateral flow chromatography, in which a test sample fluid, suspected of containing an analyte, flows (for example by capillary action) through the strip (which is frequently made of bibulous materials such as paper, nitrocellulose, and cellulose). The test fluid and any suspended analyte may flow along the strip to a detection zone in which the analyte (if present) interacts with a detection agent to indicate a presence, absence and/or quantity of the analyte. A lateral flow device may produce a test result that is qualitative or quantitative.

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,258,548; 6,555,390; 6,699,722; and 6,368,876; EP 0810436; and WO 92/12428; WO 94/01775; WO 95/16207; and WO 97/06439, each of which is incorporated by reference.

Many lateral flow devices are one-step lateral flow assays in which a biological fluid is placed in a sample area on a bibulous strip (though, non-bibulous materials may be used, and rendered bibulous by applying a surfactant to the material), and allowed to migrate along the strip until the liquid comes into contact with a chemical reagent or specific binding partner that interacts with an analyte (such as an aldehyde, glycoprotein, or glycolipid) in the liquid. Once the analyte interacts with the chemical reagent or specific binding partner, a signal (such as a fluorescent or otherwise visible dye) indicates that the interaction has occurred. Multiple discrete chemical reagents or specific binding partners may be placed on the strip (for example in parallel lines) to detect multiple analytes in the liquid. The test strips may also incorporate control indicators, which provide a signal that the test has adequately been performed, even if a positive signal indicating the presence (or absence) of an analyte is not seen on the strip.

As used herein, two solid components are in "operable contact" or "contiguous contact" when they are in contact, either directly or indirectly, in such a manner that an aqueous liquid may flow from one of the two components to the other substantially uninterruptedly, by capillarity or otherwise. Direct or contiguous contact means that the two elements are in physical contact, such as edge-to-edge or front-to-back. When two components are in direct contact, they may overlap with an overlap of about 0.5 mm to about 3 mm. However, the components may be placed with abutting edges. "Indirect contact" means that the two elements are not in physical contact, but are bridged by one or more conductors. Operable contact may also be referred to as "fluid transmitting" or "fluid continuous" contact.

As used herein, the term "sample application area" refers to an area where a fluid sample is introduced to a chromatographic test strip, such as a chromatographic test strip present in a lateral flow device. In one example, the sample may be introduced to the sample application area by external application, as with a dropper or other applicator. In another example, the sample application area may be directly immersed in the sample, such as when a test strip is dipped into a container holding a sample. In yet another example, the sample may be poured or expressed onto the sample application area.

As used herein, the terms "solid support" and "substrate" refer to any material which is insoluble, or may be made insoluble by a subsequent reaction. Numerous and varied solid supports are known to those in the art and include, without limitation, nitrocellulose, the walls of wells of a reaction tray, multi-well plates, test tubes, polystyrene beads, magnetic beads, membranes, and microparticles (such as latex particles). Any suitable porous material with sufficient porosity to allow access by detector reagents and a suitable surface affinity to immobilize capture reagents (e.g., antibodies) is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, glass or glass fibers (in some examples, these materials may be used as filters with the above polymeric materials); and mixtures or copolymers of the above classes, such as graft copolymers obtained by initializing polymerization of synthetic polymers on a pre-existing natural polymer.

The surface of a solid support may be activated by chemical processes that cause covalent linkage of an agent (e.g., a chemical reagent) to the support. However, any other suitable method may be used for immobilizing an agent (e.g., a chemical reagent) to a solid support including, without limitation, ionic interactions, hydrophobic interactions, covalent interactions and the like. A solid phase may be chosen for its intrinsic ability to attract and immobilize an agent, such as a chemical reagent. The factor may include a charged substance that is oppositely charged with respect to, for example, the chemical reagent. Except as otherwise physically constrained, a solid support may be used in any suitable shapes, such as films, sheets, strips, or plates, or it may be coated onto or bonded or laminated to appropriate inert carriers, such as paper, glass, plastic films, or fabrics. As used herein a "lateral flow substrate" is any solid support or substrate that is useful in a lateral flow device.

As used herein, the term "subject" refers to a living multicellular vertebrate organisms, a category that includes human and non-human mammals (such as laboratory or veterinary subjects).

Embodiments herein provide methods and tests for diagnosing and/or monitoring a metabolic condition such as diabetes in a subject, wherein the methods and tests measure salivary glycoproteins. In various embodiments, the methods are based on the oxidation of glycoproteins in a sample from the subject, such as saliva or urine, for example using sodium metaperiodate, and then detecting the aldehydes generated during oxidation using a chemical detection method. In various embodiments, the method is based on the finding that the specific glycoproteins oxidized in the sample, primarily sialic acid and fucose, provide an accurate measure of glycemic control when compared to traditional monitoring tools such as HbA1c and fructosamine.

This finding is unexpected because previous studies with lectin binding demonstrated that a five-member panel of lectins (e.g., *Aleuria aurantia* lectin, Concanavalin A, *Phaseolus vulgaris* agglutinin, *Datura stramonium* lectin, and *Sambucus nigra* lectin) was needed for the most accurate prediction of glycemic status. These lectins bind to sialic acid and fucose, but also mannose, galactose, and N-acetylglucosamine. By contrast, the methods disclosed herein only require detection of the oxidation products of sialic acid and fucose. An additional advantage of the method is that as a purely chemical detection method, it does not rely on lectins or antibodies to bind carbohydrate moieties present on glycoproteins.

HbA1c and fructosamine tests measure direct, non-enzymatic protein glycation. The presently disclosed methods instead measure proteins that are modified by intracellular glycosylation as opposed to non-enzymatic glycation, thus avoiding the problems associated with glycation-based tests. Hyperglycemia increases the flux of glucose through the hexosamine biosynthetic pathway, which provides the UDP-GlcNAc and GalNAc precursors for the addition of various carbohydrate moieties to proteins through both β-linked O-glycosylation of intracellular proteins as well as α-linked mucin-type O- and β-linked N-glycosylation of cell-surface and secreted proteins. O-glycosylation of intracellular proteins modulates the ability of various cells to respond to insulin, and without being bound by theory, the levels of secreted mucin-type O- and N-glycosylated proteins may reflect altered cellular metabolism due to hyperglycemia. Additionally, without being bound by theory, hyperlipidemia may regulate hexosamine biosynthetic pathway activity. Thus, the determination of glycoprotein levels in biological fluid represents a more rapid, sensitive, and inherently physiological response to metabolic control when compared to conventional glycated protein biomarkers.

While virtually all assessments of glycemic status currently employ blood samples, there are many instances in which this is not ideal, either because of patient age or attitude toward fingersticks or venipuncture, or hygiene issues in rural or underdeveloped areas. By contrast, saliva has a number of distinct advantages as a diagnostic fluid, including being non-invasive and being obtainable without special training or equipment, and it may be especially advantageous for pediatric or elderly populations and amenable to large-scale population studies. Thus, the methods disclosed herein employ salivary (and in some cases urinary) glycoprotein analysis for short-term assessment of glycemic control.

Also disclosed in various embodiments are plate assays, dipstick tests, and lateral flow devices for detecting salivary glycoproteins. In some embodiments, the tests may include a two-membrane dipstick test for detecting and/or quantifying glycosylated salivary proteins in pre-oxidized saliva samples. Other embodiments are three-membrane lateral flow devices that oxidize the glycoproteins in a salivary sample and then detect the resulting aldehydes.

EXAMPLES

Example 1

Subject Population

A total of ten subjects were recruited from a pool of 70 type-2 diabetes patients under care at Nizam's Institute of Medical Sciences, Hyderabad, India. Clinical characteristics of the subjects are shown in Table 1.

TABLE 1

| Clinical characteristics of subjects | |
|---|---|
| Participant Characteristic | Number (%) |
| Male gender | 9 (90) |
| Participant Characteristic (units) | Mean (SD) |
| Age (years) | 42.6 (16.9) |
| Body mass index (kg/m$^2$) | 26.3 (4.3) |
| Systolic blood pressure (mmHg) | 127 (15) |
| Total cholesterol (mg/dL) | 176 (42) |
| LDL (mg/dL) | 114 (35) |
| HDL (mg/dL) | 32 (7) |
| Triglycerides (mg/dL) | 148 (68) |
| Fasting plasma glucose (mg/dL) | 162 (60) |
| Hemoglobin A1c (%) | 9.3 (2.8) |
| Fasting insulin (mIU/L) | 40.5 (43.4) |
| C-peptide (ng/mL) | 1.46 (0.97) |

Subjects underwent continuous glucose monitoring (CGM) using Guardian REAL-Time monitors (Medtronic, Inc., Northridge, Calif.) for 28 continuous days with weekly study visits for device calibration and sample collection. Subjects' course of treatment for diabetes was not altered based on CGM results. The average number of BG measures obtained during the study follow-up was 6909±436 (mean±SD) per subject. Subjects were asked not to eat or smoke for at least 8 hours prior to study visits occurring between 8 AM and 9 AM on 1, 7, 14, 21, and 28 days following the baseline visit. Unstimulated saliva samples were collected at every study visit and standard blood-draws were performed at baseline and at day 28. In addition, clinical parameters, including height, weight, and blood pressure, were obtained at baseline and at the final study visit.

Example 2

Saliva and Blood Tests

Saliva samples were diluted 1:5 in 2% acetic acid, pH 4.5. Duplicate 50-μL aliquots of diluted sample were added per well of a 96-well Reacti-Bind polystyrene plate (Thermo Scientific, Rockford, Ill.) followed by 25 μL of 10 mM sodium metaperiodate (made immediately before use in 2% acetic acid, pH 4.5). The plate was agitated on a rotary shaker for 30 seconds and then covered and incubated for 10 minutes at room temperature. At the end of the incubation, 150 μl of AHMT solution (175 mg 4-Amino-3-hydrazino-5-mercapto-1,2,4-triazole in 35 ml 1N NaOH; Sigma-Aldrich, St. Louis, Mo.) was added. The plate was agitated on a rotary shaker for 30 seconds, then covered and incubated for one hour at room temperature. The absorbance at 550 nm was determined using an ELx800 plate reader (BioTek, Winooski, Vt.). Results were normalized by total protein concentration and reported in arbitrary units (AU). Blood samples were processed using an AU400e chemical analyzer (Olympus, Center Valley, Pa.) for fructosamine quantification and an HLC-723 G8 high-performance liquid chromatograph (Tosoh Bioscience, King of Prussia, Pa.) for HbA1c measurements.

Example 3

Statistical Analysis

Baseline characteristics of the subject population were tabulated as well as the 28-day change in relevant clinical parameters. One subject was missing CGM data for days 20-28 and was excluded from all CGM analyses for those days. To quantify glycemic control from the CGM data, average BG, standard deviation (SD) of BG, and mean amplitude of glycemic excursion (MAGE; 30) were calculated and matched to 7, 14, 21, and 28-day study visits. Due to the small sample size, analyses were primarily descriptive and included plots of salivary glycosylation measures across time with HbA1c, fructosamine, average BG, BG SD, and average MAGE. Pearson's correlation coefficients were computed and plotted for all measures at baseline and days 1, 7, 14, 21, and 28. An exploratory longitudinal, repeated-measures analysis was conducted to assess the ability of measured salivary glycosylation to predict average BG, BG SD, and MAGE at 7, 14, 21, and 28-day intervals and to determine the interval for which salivary glycosylation is most predictive. A secondary analysis on the effect of blood glucose variability on the relationship between average BG with fructosamine and salivary glycosylation was conducted by creating groups of high and low BG variability (according to BG SD) and correlating average BG with fructosamine and salivary glycosylation separately for each variability group. To maximize the difference in variability between the groups, the high and low BG variability groups included four subjects with the highest and lowest variability, respectively. Reported p values are two-sided. Statistical analysis was performed using SAS software, Version 9.3 of the SAS System for Windows.

Example 4

Changes in Salivary Glycosylation Reflect Different Levels of Glycemia

Figure 1B:
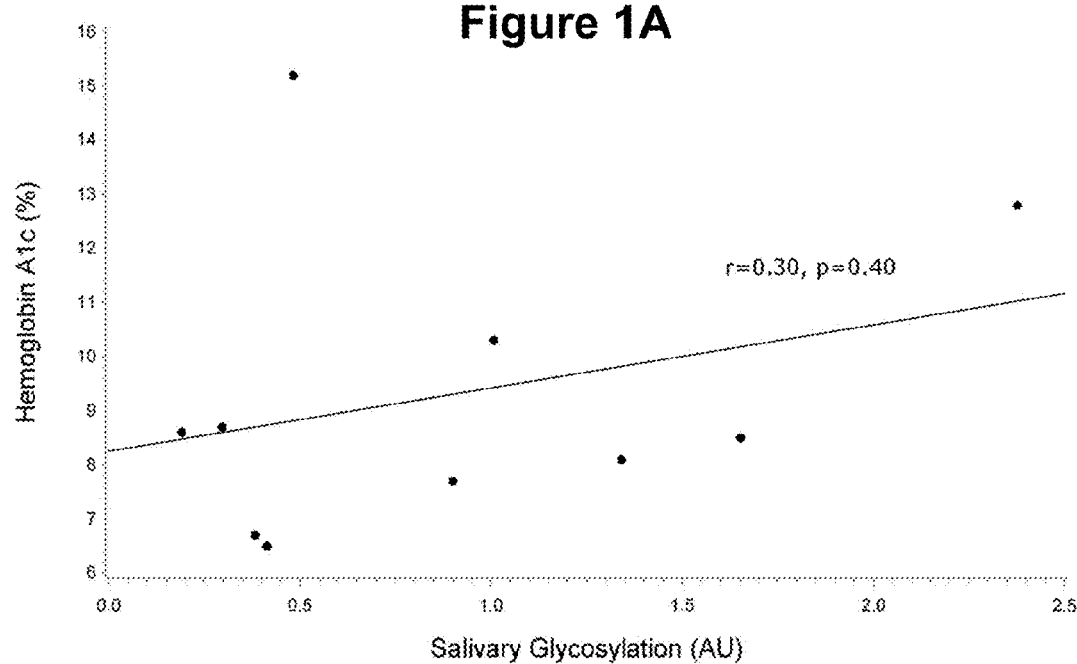

An analysis of salivary glycosylation was undertaken using the methods described above in Examples 1-4 in a series of 10 subjects with type-2 diabetes who had undergone 28 days of CGM in order to ascertain if salivary glycoprotein levels were correlated with relative glycemia. As shown in FIGS. 1A and 1B, baseline salivary glycosylation measures were strongly correlated with baseline fructosamine values (FIG. 1A; r=0.65, p=0.06), and moderately correlated with HbA1c (FIG. 1B; r=0.30, p=0.40). Salivary glycosylation was strongly correlated with fructosamine and moderately correlated with hemoglobin A1c.

Figure 2:
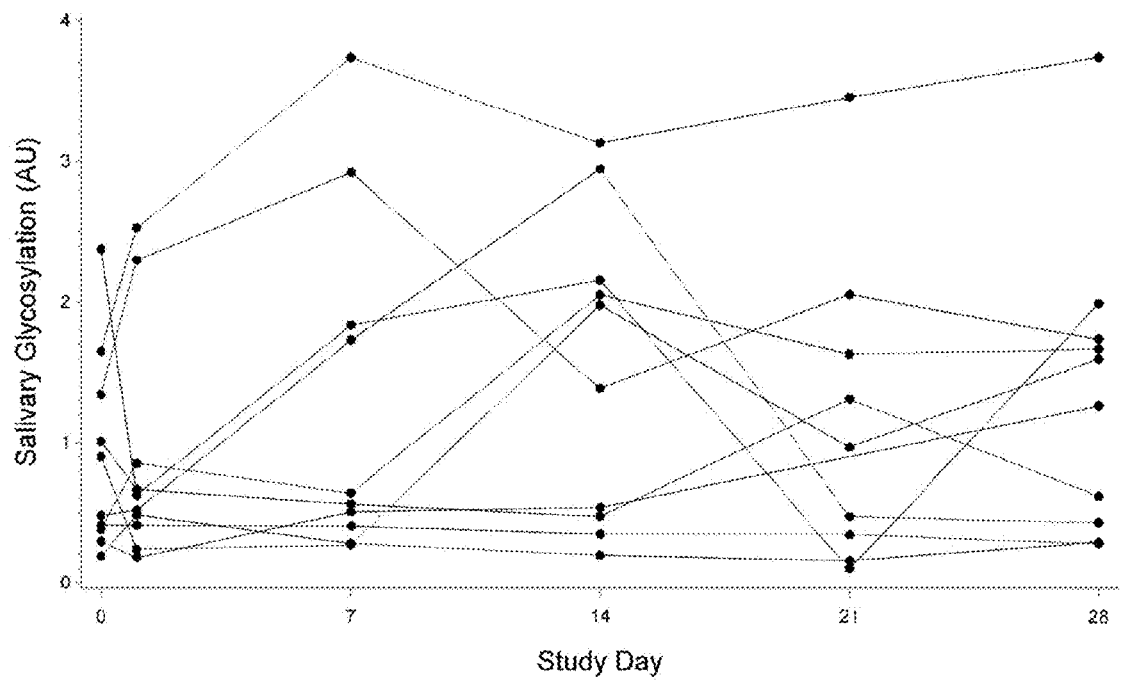
FIG. 2 is a graph illustrating salivary glycosylation in subjects over time, wherein weekly salivary glycosylation is plotted against study day for ten participants, in accordance with various embodiments.

Longitudinal values of salivary glycosylation were plotted over time to analyze the range and variability in these subjects (FIG. 2). Salivary glycosylation mean, SD, and range were calculated for each subject and are shown below in Table 2. To measure the relationship between the variability in salivary glycosylation and variability in BG, SD salivary glycosylation was correlated with SD BG over all available data, and a strong correlation was found between the two measures (r=0.56, p=0.12).

TABLE 2

Descriptive statistics of salivary glycosylation by subject

| Subject | Mean Salivary Glycosylation (AU) | Standard Deviation | Range |
|---|---|---|---|
| 1 | 1.51 | 0.92 | 0.10-2.38 |
| 2 | 1.96 | 0.60 | 1.34-2.92 |
| 3 | 0.37 | 0.05 | 0.28-0.41 |
| 4 | 3.04 | 0.82 | 1.65-3.74 |

TABLE 2-continued

Descriptive statistics of salivary glycosylation by subject

| Subject | Mean Salivary Glycosylation (AU) | Standard Deviation | Range |
|---|---|---|---|
| 5* | 0.56 | 0.42 | 0.18-1.26 |
| 6 | 1.20 | 0.67 | 0.38-2.05 |
| 7 | 0.99 | 0.70 | 0.24-1.98 |
| 8 | 1.10 | 1.04 | 0.43-2.95 |
| 9 | 0.77 | 0.32 | 0.48-1.31 |
| 10 | 0.27 | 0.12 | 0.16-0.49 |

*Subject 5 was missing day-21 salivary glycosylation data.

Figure 3A:
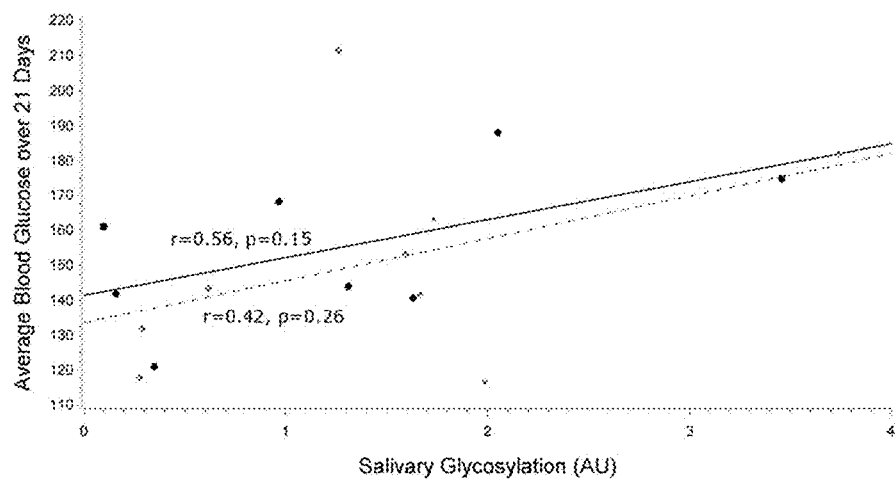
FIGS. 3A, 3B, and 3C are three graphs illustrating the relationship between salivary glycosylation and average BG, BG SD, and mean amplitude of glucose excursion (MAGE) over 21-day periods, wherein salivary glycosylation is plotted against 21-day average blood glucose (FIG. 3A), blood glucose standard deviation (FIG. 3B), and MAGE (FIG. 3C) for study days 21 and 28, in accordance with various embodiments.
Figure 3B:
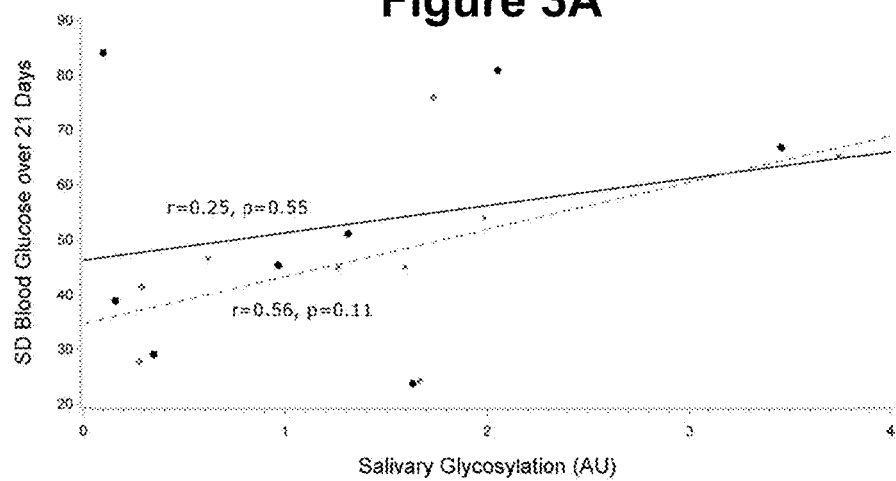
Figure 3C:
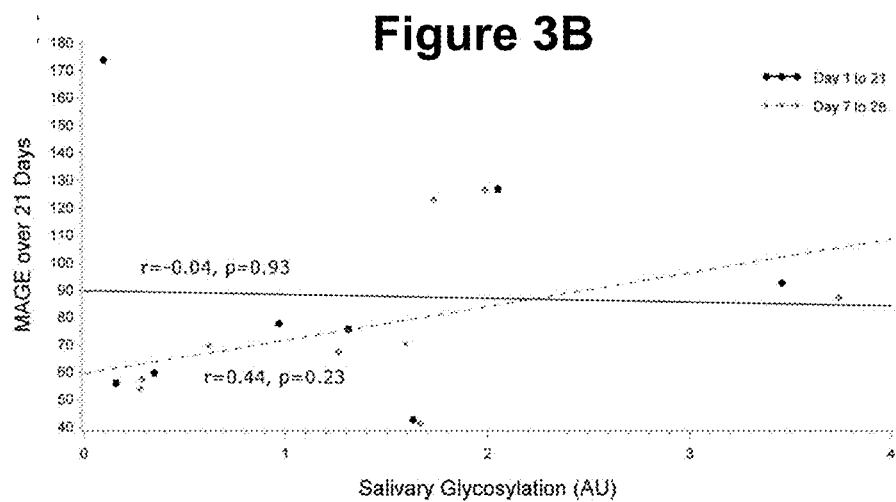

Pearson's correlation coefficients and corresponding p-values for correlation of salivary glycosylation measurements with average BG, BG SD, and MAGE across 7, 14, 21, and 28 days indicated that the strongest relationship was between salivary glycosylation and average BG over 21 days (r=0.56, p=0.23 at day 21 and r=0.42, p=0.26 at day 28). Results from this analysis are displayed in FIGS. 3A, 3B, and 3C, which illustrate the relationship between salivary glycosylation and average BG, BG SD, and mean amplitude of glucose excursion (MAGE) over 21-day periods, wherein salivary glycosylation is plotted against 21-day average blood glucose (FIG. 3A), blood glucose standard deviation (FIG. 3B), and MAGE (FIG. 3C) for days 21 and 28, in accordance with various embodiments. The results of an exploratory longitudinal, repeated-measure analysis confirmed this finding, with salivary glycosylation having a significant longitudinal relationship with average BG over 21 days (p<0.01). Salivary glycosylation was strongly correlated with average blood glucose for both study days 21 and 28, but was weakly correlated with both blood glucose standard deviation and MAGE, except at day 28 where it was strongly correlated with blood glucose standard deviation.

Figure 4A:
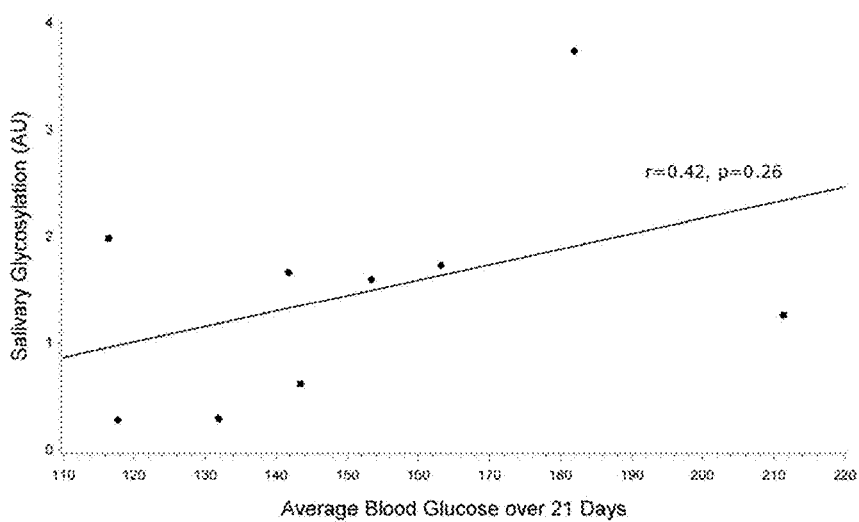
FIGS. 4A, 4B, and 4C illustrate a comparison of 21-day average BG with salivary glycosylation, fructosamine and HbA1c, wherein the average blood glucose over 21 days is plotted against salivary glycosylation (FIG. 4A), fructosamine (FIG. 4B), and hemoglobin A1c (FIG. 4C) for study day 28, in accordance with various embodiments.
Figure 4B:
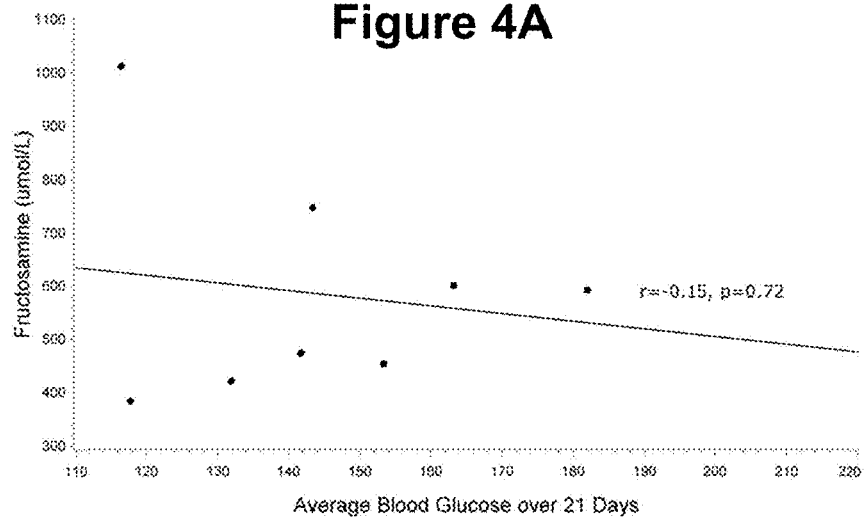
Figure 4C:
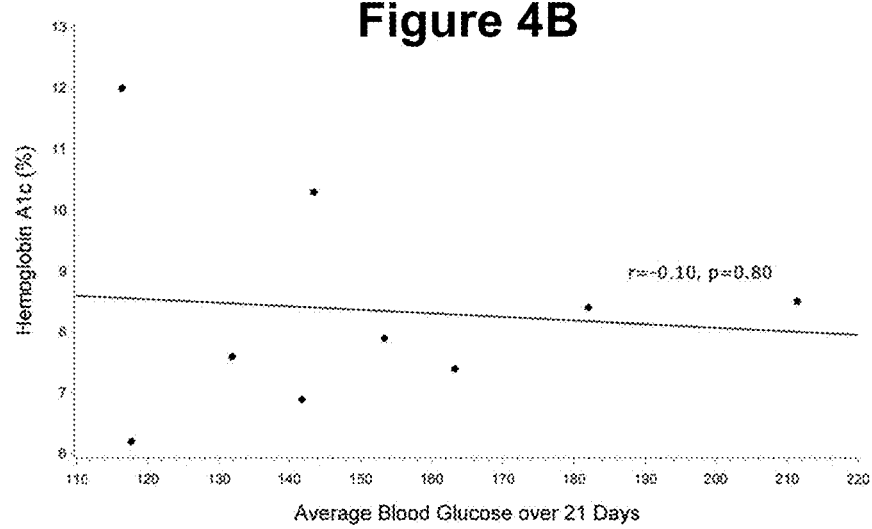

CGM measures of glycemic control were correlated with measures of salivary glycosylation, fructosamine, and HbA1c. FIGS. 4A, 4B, and 4C illustrate a comparison of 21-day average BG with salivary glycosylation, fructosamine and HbA1c, wherein the average blood glucose over 21 days is plotted against salivary glycosylation (FIG. 4A), fructosamine (FIG. 4B), and hemoglobin A1c (FIG. 4C) for study day 28, in accordance with various embodiments. As shown in FIGS. 4A, 4B, and 4C, salivary glycosylation measures demonstrated stronger correlation with average BG over 21 days than did HbA1c or fructosamine. There was a strong positive relationship between salivary glycosylation and average blood glucose. Average blood glucose was poorly correlated with fructosamine and hemoglobin A1c. Table 3 provides the Pearson's correlation coefficients for average BG, BG SD, and MAGE over 21 days with day-28 salivary glycosylation, fructosamine, and HbA1c. Salivary glycosylation was the strongest predictor of average BG and BG SD compared to fructosamine and HbA1c, while fructosamine was the strongest predictor of MAGE.

TABLE 3

Day 28 correlation of 21-day average blood glucose with salivary glycosylation, fructosamine, and HbA1c.

| Measure of glycemia (units) | Average BG | | BG SD | | MAGE | |
|---|---|---|---|---|---|---|
| | Pearson's correlation coefficient | p-value | Pearson's correlation coefficient | p-value | Pearson's correlation coefficient | p-value |
| Salivary glycosylation (AU) | 0.42 | 0.26 | 0.56 | 0.12 | 0.44 | 0.23 |
| Fructosamine (mmol/L) | −0.15 | 0.72 | 0.43 | 0.29 | 0.73 | 0.04* |
| Hemoglobin A1c (%) | −0.10 | 0.80 | 0.33 | 0.39 | 0.57 | 0.11 |

*$p < 0.05$

Figure 5A:
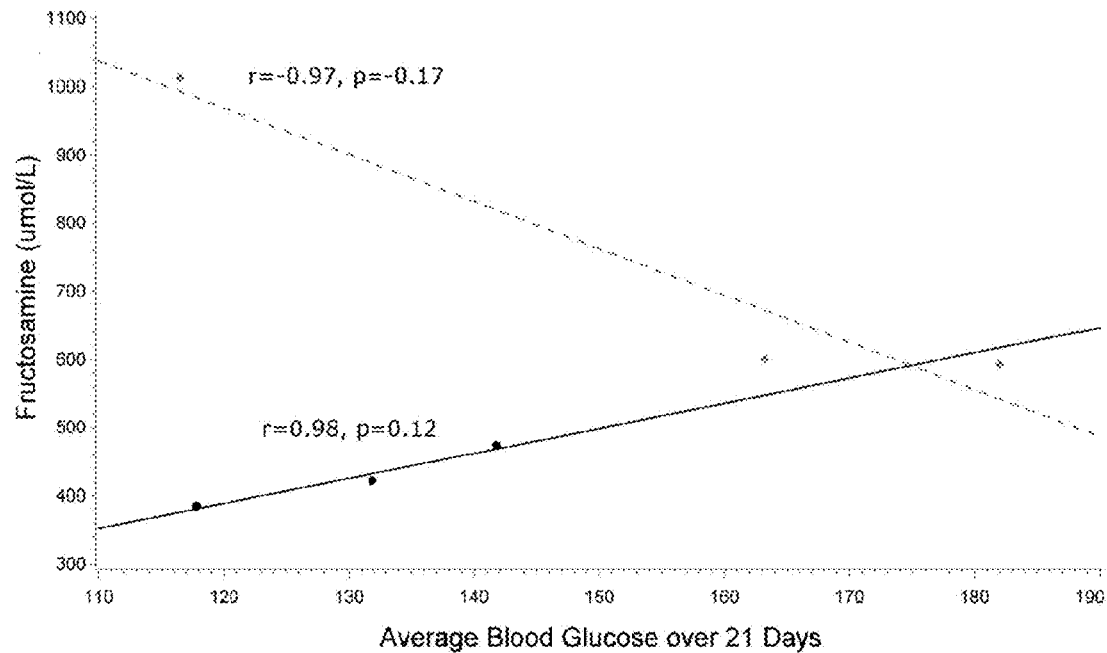
FIGS. 5A and 5B illustrate a correlation of 21-day average blood glucose and fructosamine by subjects with low and high blood glucose variability, wherein the average blood glucose is correlated with fructosamine (FIG. 5A) and salivary glycosylation (FIG. 5B) for individuals with low and high blood glucose variability, in accordance with various embodiments.
Figure 5B:
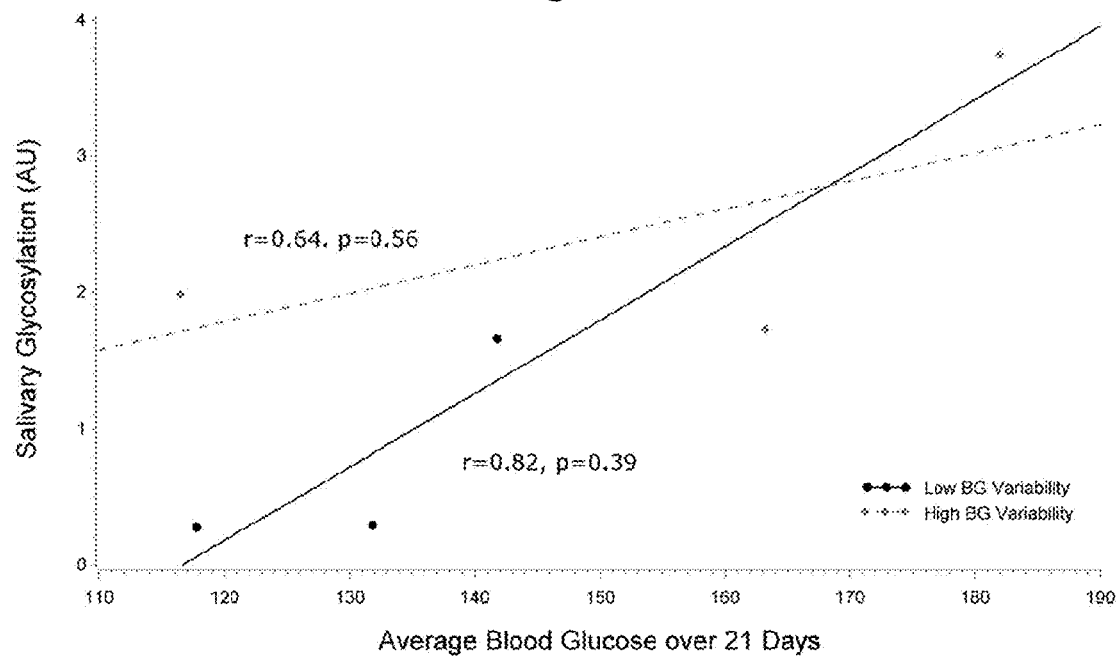

A sub-analysis was performed to determine if the relationship of salivary glycosylation and fructosamine with average BG was mediated by BG variability. Subjects in the low-variability group had an average BG SD of 31 mg/dL, while subjects in the high-variability group had a BG SD of 65 mg/dL. For subjects in the low-variability group, fructosamine was a strong predictor (r=0.98) of average blood glucose; however, for the high-variability group, increases in fructosamine strongly predicted decreases in average BG, directly opposite of what would be clinically expected. Salivary glycosylation was a strong predictor of average BG in both the low- and high-variability group (r=0.82, r=0.64), and this was not greatly affected by BG variability. FIGS. 5A and 5B illustrate these relationships. More specifically, FIGS. 5A and 5B illustrate a correlation of 21-day average blood glucose and fructosamine by subjects with low and high blood glucose variability, wherein the average blood glucose is correlated with fructosamine (FIG. 5A) and salivary glycosylation (FIG. 5B) for individuals with low and high blood glucose variability, in accordance with various embodiments. Increased blood glucose variability weakened the relationship of average blood glucose with fructosamine, but not with salivary glycosylation, in accordance with various embodiments.

Figure 6A:
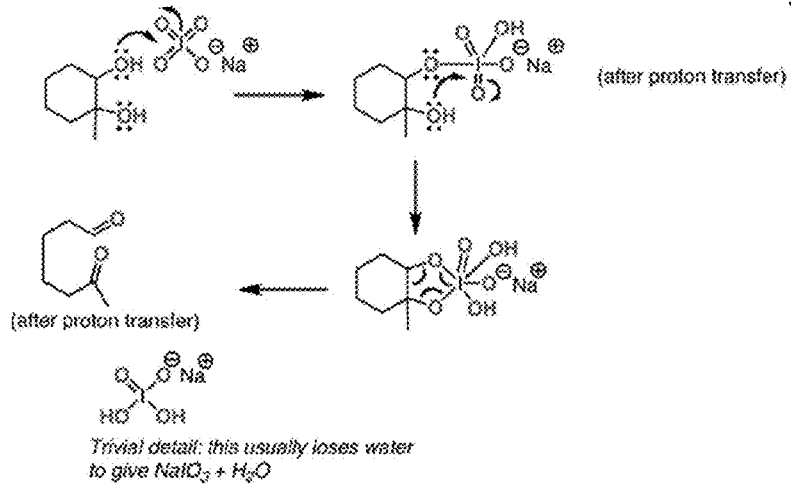
FIGS. 6A and 6B illustrate the two chemical reactions involved in the salivary glycosylation methods described herein, the periodate oxidation of vicinal diols that generates aldehydes (FIG. 6A), and the 4-amino-3-hydrazino-5-mercapto-1,2,4-triazole reactivity with aldehydes (AHMT) (FIG. 6B), in accordance with various embodiments.
Figure 6B:
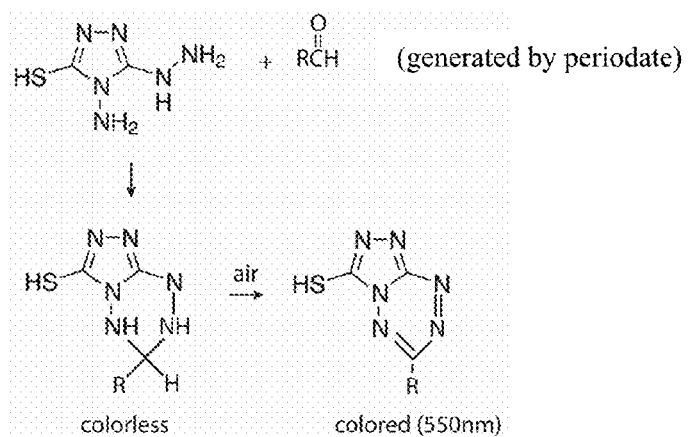

In the methods described above, sialic acid and fucose are readily oxidized to generate aldehydes, and FIGS. 6A and 6B illustrate the two chemical reactions involved in the salivary glycosylation methods described herein: the periodate oxidation of vicinal diols that generates aldehydes (FIG. 6A), and the 4-amino-3-hydrazino-5-mercapto-1,2,4-triazole reactivity with aldehydes (AHMT) (FIG. 6B), which reaction generates a color change, for instance that may be detected visually or with a colorimeter.

Example 5

Salivary Protein Glycosylation Test for Diagnosis and Monitoring of Diabetes

The array of approaches to determine glycemic control ranges from purely glucose-based parameters such as random BG testing routinely employed by individuals with type-1 diabetes and fasting BG and oral glucose tolerance tests to assess impaired fasting glucose or impaired glucose tolerance in pre-diabetes and type-2 diabetes, to indices of hyperglycemia-induced protein glycation (HbA1c, fructosamine, and glycated albumin) and reabsorption of 1,5-anhydroglucitol. Glycemic variability has emerged as a potentially important aspect of monitoring glycemic control that may be more associated with the development of complications such as cardiovascular disease than average BG levels. Although the clinical utility of assessing glycemic variability in routine screening or monitoring remains controversial, the effect of glycemic variability on the performance of assays for average BG is important, as discussed below. The existing assays for long and short-term average glycemia have several disadvantages, notably the inability of HbA1c to reflect intrinsic variability in glucose levels in individual patients and discrepancies in the average glucose levels derived from different measurements (the so-called glycation gap).

Described herein is an alternative parameter of glycemia (total protein glycosylation) that is driven by cellular metabolism and that is discernible in saliva. Specifically, baseline salivary glycosylation measures are strongly correlated with fructosamine (r=0.65), a measure of 2 to 4-week glycemic control. Additionally, compared to HbA1c and fructosamine, salivary glycosylation measures were better predictors of average BG and SD BG over a 21-day interval. Furthermore, salivary glycosylation measures exhibited a stronger correlation with measures of glycemic control than fructosamine or HbA1c, and in terms of predicting hyperglycemia, the accuracy of fructosamine was affected by BG variability, while the accuracy of salivary glycosylation was not.

Thus, salivary glycosylation is a powerful alternative biomarker for recent hyperglycemia, as it has better ability to predict 21-day blood glucose measures than HbA1c or fructosamine. Additionally, the ability to use saliva rather than blood constitutes a separate, significant advantage for salivary glycosylation. An important use for a non-invasive indicator of short-term glycemia would be to allow patients on therapy to more conveniently monitor their glycemic control. This may increase the currently low rate of adherence to diabetes medications, an increase in which would have the potential for significant healthcare cost savings.

Example 6

Plate Assay

Figure 7A:
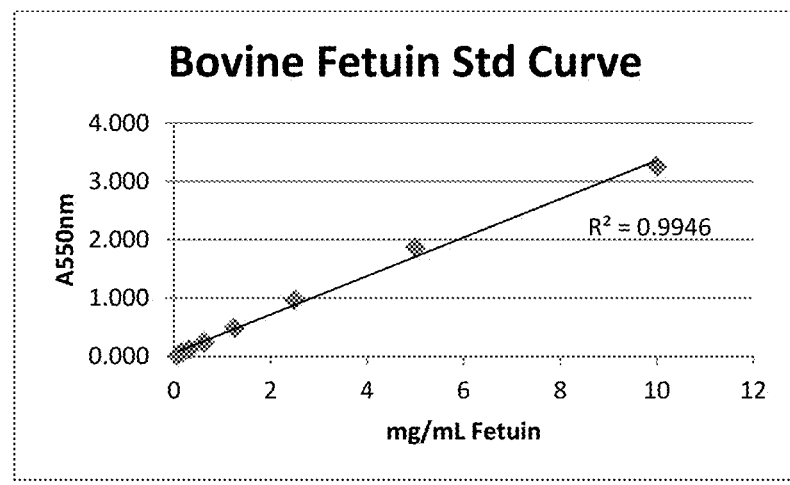
FIGS. 7A and 7B are two graphs illustrating the accuracy of the salivary total glycosylation plate assay, comparing the bovine fetuin standard curve (FIG. 7A) with the saliva total glycosylation (FIG. 7B), in accordance with various embodiments.
Figure 7B:
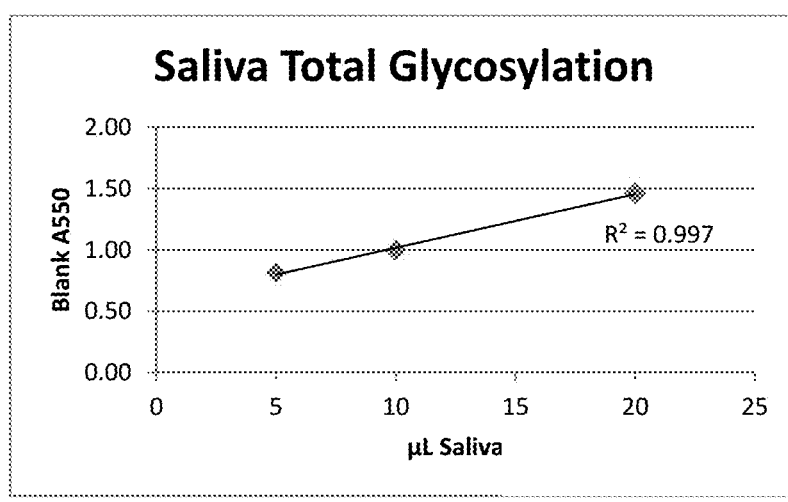

FIGS. 7A and 7B are two graphs illustrating the accuracy of the salivary total glycosylation plate assay, comparing the bovine fetuin standard curve (FIG. 7A) with the saliva total glycosylation (FIG. 7B), in accordance with various embodiments;

In one specific, non-limiting example, the plate assay may be carried out as follows:
1. Add 40 μl 2% HOAc pH 4.5 into sample wells
2. Place 50 μl standards and 10 μl samples into appropriate wells
3. Prepare immediately before use and add 25 μl NaIO$_4$ solution (10 mM, or 21.4 mg/10 mL assay buffer)
4. Mix for 30 seconds and cover and incubate for 10 minutes at room temperature
5. Prepare immediately before use and add 150 μl AHMT (34 mM, or 175 mg into 35 mL 1N NaOH)
6. Mix for 30 seconds and then cover and incubate for 60 minutes at room temperature
7. Read at A550 nm Example 7

Creation of a Dipstick Test

Although the assays described above in Examples 1-6 produce accurate results that correlate well with a 21 day average glucose, in some embodiments, a dipstick-based test may be more desirable for point-of-care use than a liquid based assay carried out in a microtiter plate. Thus, in some embodiments, the disclosed methods may be carried out using a dipstick-based test. However, in various embodiments, adapting the plate assay to be used in a dipstick format may be challenging. For example, immobilization of AHMT requires the selection of the optimal membrane substrate (in all, more than 50 different membranes were evaluated and only a few proved adequate), the optimal reagent concentration, and the optimal reaction time, and the stability of the colorimetric result may be difficult to achieve, as well. In some embodiments, incorporation of periodate and alkali into the membrane may be challenging, as well.

Figure 8A:
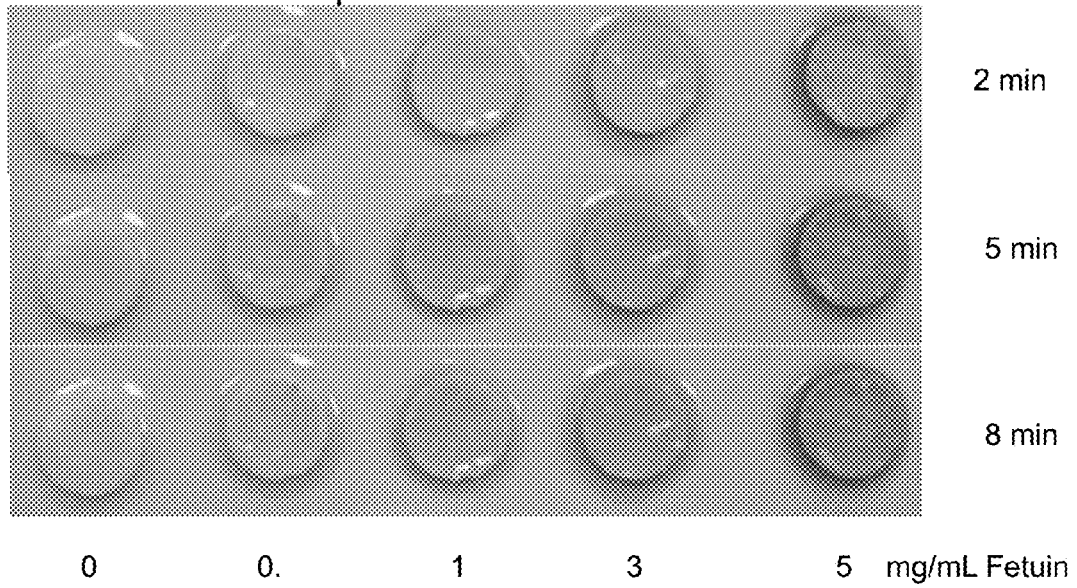
FIGS. 8A and 8B are a digital image (FIG. 8A) and a graph (FIG. 8B) illustrating an example of a solid phase assay, in accordance with various embodiments.
Figure 8B:
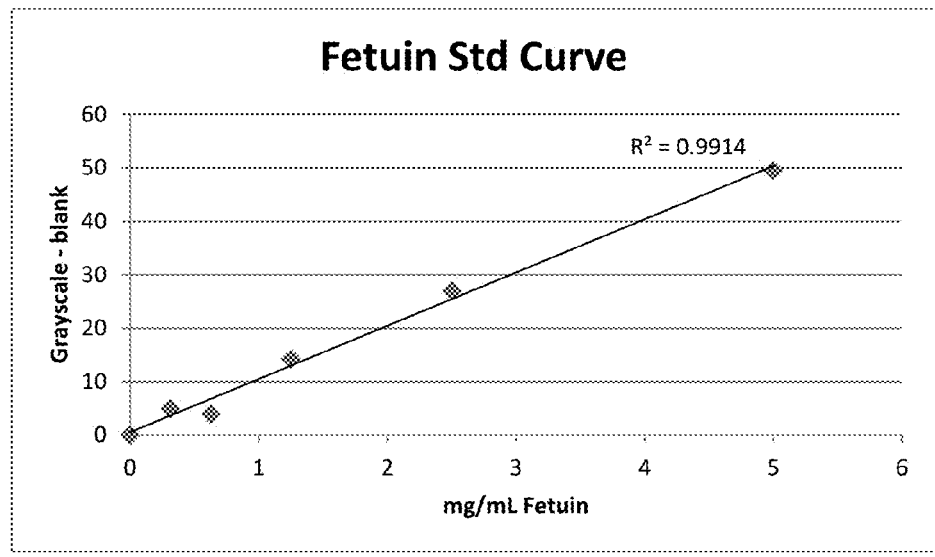
Figure 9A:
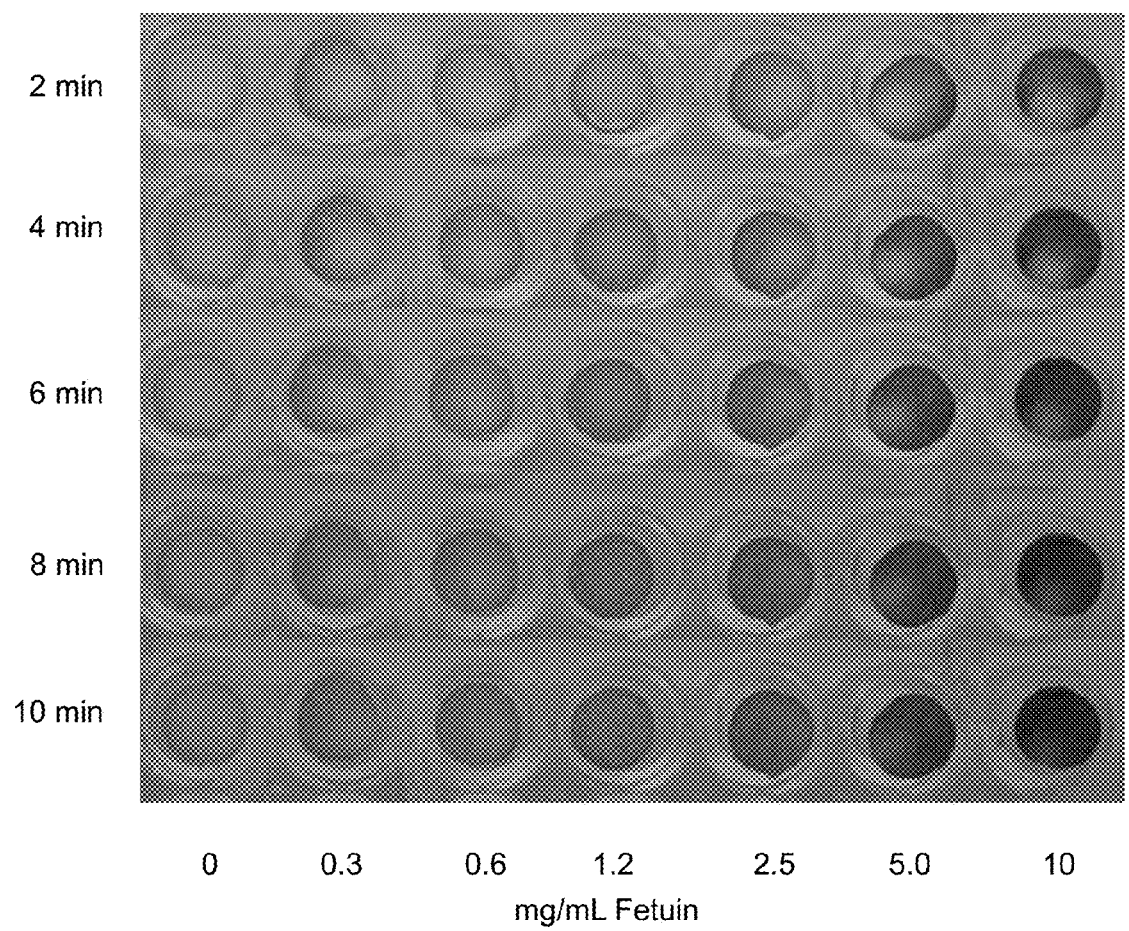
FIGS. 9A and 9B are a digital image (FIG. 9A) and a graph (FIG. 9B) illustrating the color change time course for the solid phase assay, in accordance with various embodiments.
Figure 9B:
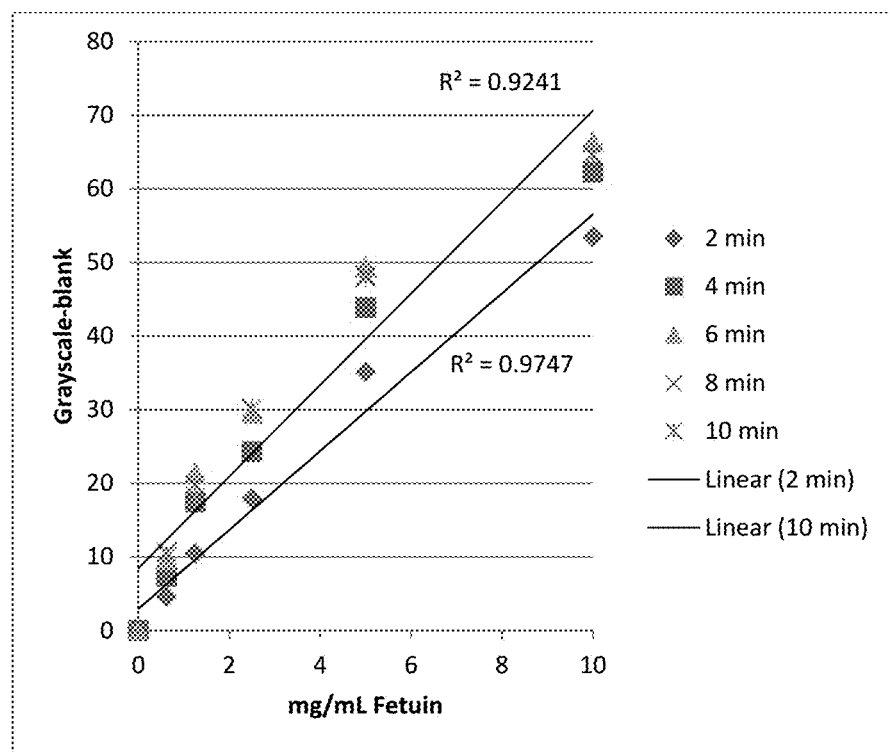

FIGS. 8A and 8B are a digital image (FIG. 8A) and a graph (FIG. 8B) illustrating an example of a solid phase prototype assay, in accordance with various embodiments. In the example illustrated in FIG. 8, a solid phase test was created by immobilizing AHMT on a membrane (VWR 698 glass fiber membrane was saturated with a solution of 0.2 g AHMT dissolved in 20 mL DMSO, blotted, then dried at 50° C. for one hour). The sample was oxidized, and 20 μL of sample was added to each membrane, followed by 25 μL 2 N NaOH. FIGS. 9A and 9B are a digital image (FIG. 9A) and a graph (FIG. 9B) illustrating the color change time course for the solid phase assay, in accordance with various embodiments.

In some embodiments, a two-membrane dipstick test may be used in place of the solid phase assay depicted in FIGS. 8 and 9. In an exemplary two-membrane dipstick test, a membrane device is used that includes an AHMT membrane and an alkali membrane. Surprisingly, simple aqueous solutions of NaOH do not work when dried on a membrane. However, when 80% aqueous Ethanol was used as the solvent for NaOH, the resulting membrane greatly improved the reaction speed. The oxidation step is carried out for thirty seconds before application of the sample to the dipstick membranes, the sample is added to the membrane, and the dipstick is read using a colorimeter after five minutes.

Figures 13A, 13B:
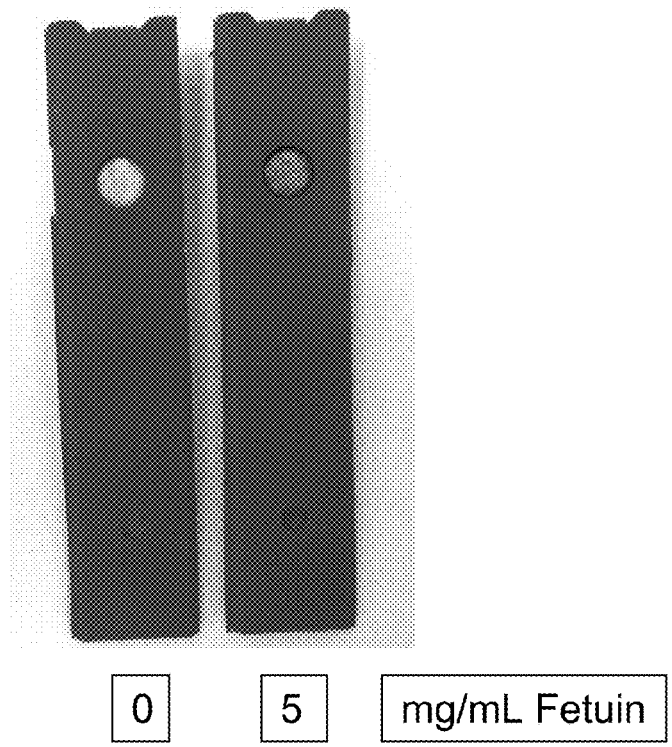
FIGS. 13A and 13B illustrate a table showing a comparison of three examples of a three-membrane (one-step) saliva test strip having sodium periodate concentrations of 30, 50, and 100 mg/10 mL of buffer, and their efficacy (measured in percent reflectance) at detecting fetuin (FIG. 13A), and a digital image of two examples of a three-membrane saliva test strip showing negative and positive controls, in accordance with various embodiments.

In some embodiments, a three-membrane dipstick test may be used in place of the solid phase assay depicted in FIGS. 8 and 9. In an exemplary three-membrane dipstick test, a membrane device is used that includes an AHMT membrane, an alkali membrane, and a sodium metaperiodate membrane. Solutions of sodium metaperiodate in acetic acid did not perform well when dried on membranes, and sodium metaperiodate in MES buffer, pH 5 (commonly used for glycoprotein oxidation studies) produced unacceptably high background signal in the absence of glycoprotein. However, sodium metaperiodate dissolved in 50 mM sodium phosphate, pH 5.5 works well and is stable when dried on VWR 692 glass fiber membrane. FIGS. 13A and 13B are a table and a digital image demonstrating the feasibility of a one-step assay.

In contrast with the liquid plate assay described above in Example 6, which requires making a fresh solution of AHMT in NaOH immediately prior to use, the two-membrane dipstick test circumvents this problem by including two separate membranes separated by a mesh layer, one with immobilized AHMT and the other with NaOH. In various embodiments, the two membranes cannot make intimate contact with one another, or the AHMT will be inactivated. Therefore, the mesh separator is used to prevent intimate contact between the membranes.

Whereas the liquid assay requires 60 minutes of incubation with AHMT following periodate oxidation, the solid phase assay only requires 5-10 minutes. The initial adduct of aldehyde with AHMT is colorless, and only after subsequent oxidation by O2 from air does it turn purple. This process is diffusion-limited, and the high surface area of the membranes where the AHMT is immobilized facilitates this portion of the reaction.

Additionally, the selection of membranes is important. In various embodiments, the membranes must be chosen to not react with periodate, AHMT, or NaOH, and they require sufficient porosity to allow flow from one membrane to the other.

Figure 10A:
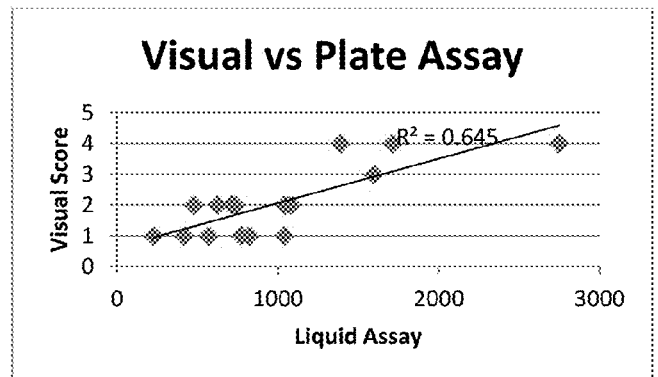
FIGS. 10A, 10B, and 10C illustrate a comparison of plate and dipstick assays, including a graph showing a comparison of the visual assay and the plate assay (FIG. 10A), a comparison of the dipstick assay and the plate assay (FIG. 10B), and a comparison of the dipstick assay, the plate assay, and CGMS samples (FIG. 10C), in accordance with various embodiments.
Figure 10B:
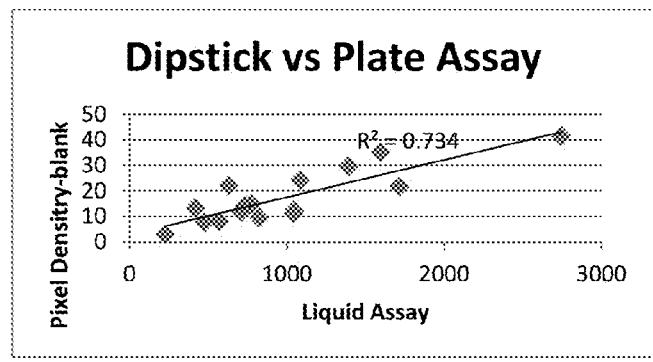
Figure 10C:
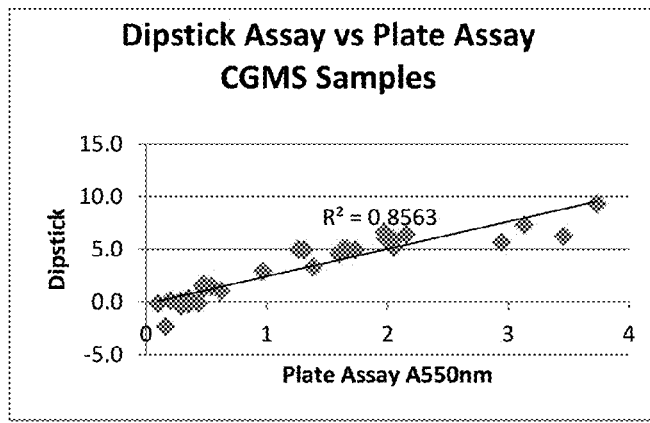
Figure 11A:
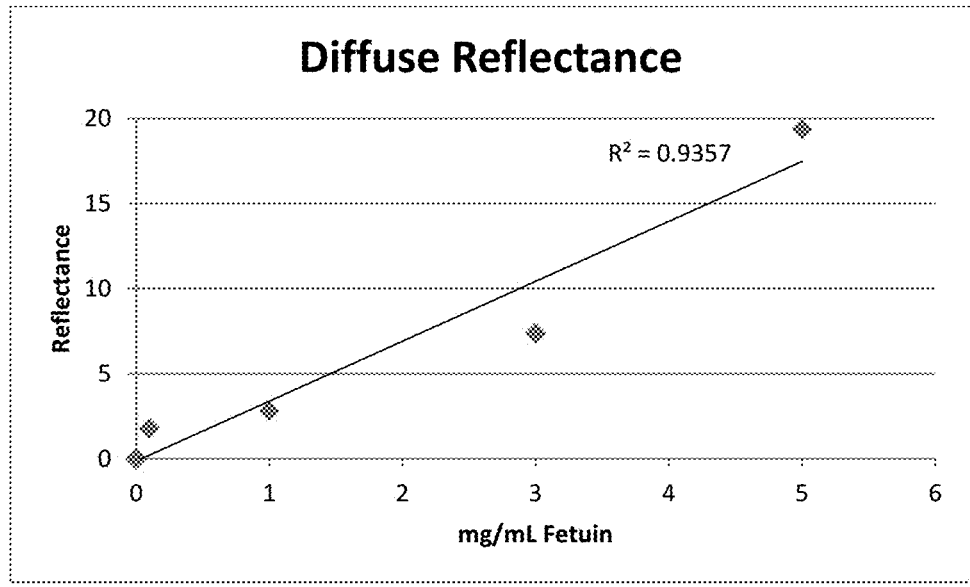
FIGS. 11A and 11B illustrate a summary graph of the dipstick test (FIG. 11A), and a schematic diagram of an example of the two-membrane dipstick test (FIG. 11B), in accordance with various embodiments.
Figure 11B:
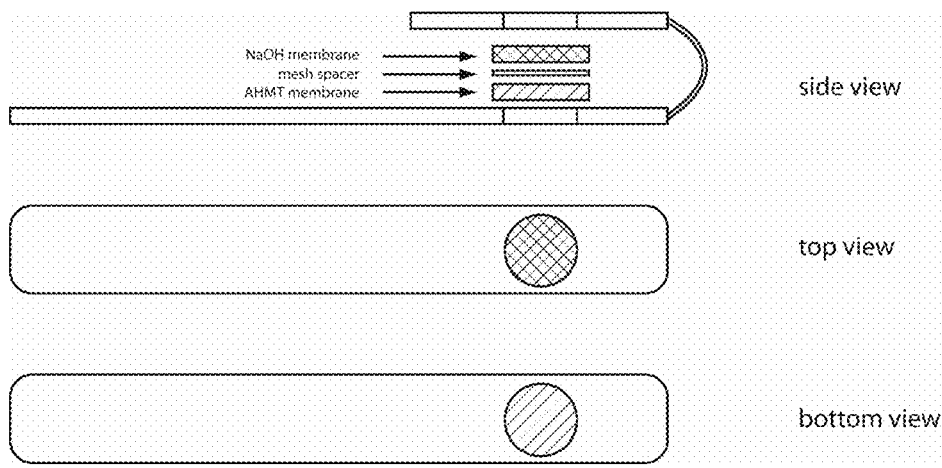

FIGS. 10A, 10B, and 10C illustrate a comparison of plate and dipstick assays, including a graph showing a comparison of the solid phase assay and the plate assay (FIG. 10A), a comparison of the dipstick assay and the plate assay (FIG. 10B), and a comparison of the dipstick assay, the plate assay, and CGMS samples (FIG. 10C). FIGS. 11A and 11B illustrate a summary graph of the dipstick test (FIG. 11A), and a schematic diagram of an example of the two-membrane dipstick test (FIG. 11B), in accordance with various embodiments. In the embodiment illustrated in FIG. 11B, two separate membranes are in operable contact with each other and separated by a mesh layer, one with immobilized AHMT and the other with NaOH. In various embodiments, the mesh separator is used to prevent intimate contact between the membranes, thereby preventing inactivation of the AHMT.

Figure 12A:
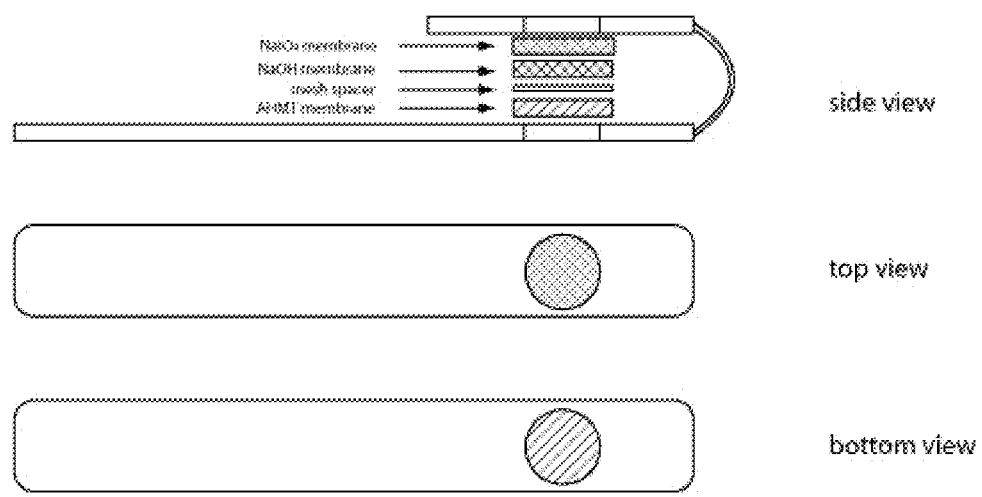
FIGS. 12A and 12B illustrate schematic diagram of an example of a three-membrane, one-step lateral flow test (FIG. 12A) and a color chart for interpreting test results (FIG. 12B), in accordance with various embodiments.
Figure 12B:
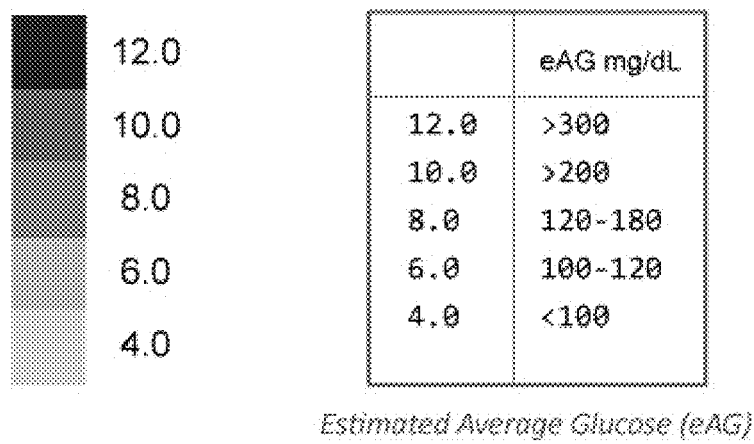

FIGS. 12A and 12B illustrate schematic diagram of an example of a one-step lateral flow test (FIG. 12A) and a color chart for interpreting test results (FIG. 12B), in accordance with various embodiments. In the illustrated embodiment, the sample is applied to a sample application area and flows to (or is applied directly to) a NaIO$_4$ membrane (e.g., a first membrane), where the glycosylated proteins in the sample are chemically oxidized. The oxidation products (primarily oxidized sialic acid and fucose) then pass to a second membrane with immobilized NaOH, through a mesh separator, and to a third membrane having AHMT immobilized thereupon. In various embodiments, the mesh separator is used to allow operable contact between the second and third membranes but to prevent intimate contact therebetween, thereby preventing inactivation of the AHMT.

FIGS. 13A and 13B illustrate a table showing a comparison of three examples of a three-membrane (one-step) saliva test strip having sodium periodate concentrations of 30, 50, and 100 mg/10 mL of buffer, and their efficacy (measured in percent reflectance) at detecting fetuin (FIG. 13A), and a digital image of two examples of a three-membrane saliva test strip showing negative and positive controls, in accordance with various embodiments. The exemplary test strips readily distinguish between the negative control (0 mg/ml fetuin) and the positive control (5 mg/ml fetuin).

Example 8

Methods of Determining a Glycemic State in a Subject

In various embodiments, the disclosed methods and test devices may be used to determine a glycemic state in a subject, for instance, diagnosing a metabolic condition such as diabetes, pre-diabetes, or gestational diabetes in a subject, or determining a degree of glycemic control in a subject. In some embodiments, s saliva sample may be obtained from a subject and subjected to the methods disclosed herein or applied to a test device as disclosed herein, such as a lateral flow device. In some embodiments, the sample may be oxidized and then applied to a dipstick (two-membrane) test as disclosed herein.

The methods and test devices described herein may produce a quantifiable result that may be assessed visually or with the aid of a colorimetric reading device. Once a result is obtained, it may be compared with a standard, such as the example shown in FIG. 12B. A result that is significantly higher than an established normal reference range may indicate that the subject has diabetes, pre-diabetes, or gestational diabetes.

In some embodiments, the disclosed methods and tests may be used to monitor a glycemic state in a subject, for instance to establish a baseline degree of glycemic control (e.g., a single point measurement that corresponds with an average blood glucose value for the preceding three week period), or to monitor changes in glycemic control over time (e.g., to determine whether glycemic control has improved or deteriorated over a period of time or in response to a change in therapy). In this example, a test result that is higher than a previous test result may indicate worsening glycemic control, wherein a test result that is lower than a previous test result may reflect an improvement in glycemic control. In various embodiments, the test may be repeated periodically, such as every three weeks, every six weeks, every three months, every four months, every six months, or yearly.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments illustrated and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A method of determining a glycemic state in a subject, the method comprising: chemically oxidizing a saliva sample from the subject, thereby oxidizing one or more glycoproteins in the saliva sample to generate one or more oxidation products, wherein the one or more oxidation products comprise one or more aldehydes;
quantifying the one or more aldehydes in the oxidized saliva sample; and
comparing a level of the one or more aldehydes to a normal control value, wherein an increase in the level of the one or more aldehydes indicates that the subject has an elevated glycemic state.

2. The method of claim 1, wherein determining the glycemic state in the subject comprises determining an average blood glucose value for the subject.

3. The method of claim 2, wherein the average blood glucose value is a three-week average blood glucose value.

4. The method of claim 1, wherein the method is a method of diagnosing diabetes in the subject, and wherein the subject is determined to have diabetes if the level of the one or more aldehydes exceeds the normal control value.

5. The method of claim 2, wherein the method is a method of monitoring glycemic control in the subject.

6. The method of claim 1, wherein oxidizing the saliva sample comprises reacting the saliva sample with sodium metaperiodate.

7. The method of claim 1, wherein oxidizing the saliva sample comprises applying the saliva sample to a sodium metaperiodate membrane.

8. The method of claim 1, wherein quantifying aldehydes in the oxidized saliva sample comprises using a chemical detection method.

9. The method of claim 1, wherein the one or more glycoproteins comprise sialic acid and fucose.

10. A lateral flow device for detecting glycoproteins in a saliva sample, the lateral flow device comprising:
a first membrane comprising sodium metaperiodate;
a second membrane in operable contact with the first membrane, the second membrane comprising NaOH;
a third membrane in operable contact with the second membrane, the third membrane comprising immobilized 4-amino-3-hydrazino-5-mercapto-1,2,4-triazole (AHMT); and
a mesh layer disposed between the second membrane and the third membrane.

11. The lateral flow device of claim 10, wherein the first membrane oxidizes sialic acid and fucose in the saliva sample.

12. The lateral flow device of claim 11, wherein the third membrane detects aldehydes in the oxidized saliva sample.

13. The lateral flow device of claim 12, wherein the third membrane produces a colorimetric result corresponding to a quantity of aldehydes in the oxidized saliva sample.

14. A kit for detecting glycoproteins in a saliva sample, the kit comprising:
a reagent for oxidizing glycoproteins in a saliva sample;
a test strip for detecting aldehydes in an oxidized saliva sample, the test strip comprising:
a first membrane comprising NaOH;
a second membrane in operable contact with the first membrane, the second membrane comprising immobilized 4-amino-3-hydrazino-5-mercapto-1,2,4-triazole (AHMT);
a mesh layer disposed between the first membrane and the second membrane, and
instructions for using the kit.

15. The kit of claim 14, wherein the reagent for oxidizing glycoproteins in the saliva sample comprises sodium metaperiodate.

16. The kit of claim 14, wherein the reagent for oxidizing glycoproteins in the saliva sample comprises a membrane that comprises sodium metaperiodate, wherein the membrane that comprises sodium metaperiodate is in operable contact with the first membrane.

17. The kit of claim 14, further comprising a colorimeter for reading the test strip.

18. The kit of claim 17, wherein the colorimeter generates a number corresponding to an amount of aldehydes detected by the test strip.

19. The kit of claim 18, wherein the number corresponding to the amount of aldehydes detected by the test strip ranges from 4.0-12.0, and wherein a number higher than 6.0 reflects an elevated average blood glucose value compared to a normal average blood glucose value.

* * * * *